（12) United States Patent
Haider (10) Patent No.: US 6,565,510 B1
(45) Date of Patent: May 20, 2003

(54) METHOD AND APPARATUS FOR SERVICING REMOTE ULTRASOUND BEAMFORMER FROM CENTRAL SERVICE FACILITY

(75) Inventor: Bruno Hans Haider, Ballston Lake, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/532,316

(22) Filed: Mar. 22, 2000

(51) Int. Cl.[7] ................................................ A61B 8/00
(52) U.S. Cl. ...................................... 600/437; 600/447
(58) Field of Search .................................. 600/437–472

(56) References Cited

U.S. PATENT DOCUMENTS

| | | | | |
|---|---|---|---|---|
| 5,517,994 A | * | 5/1996 | Burke et al. ................. | 600/437 |
| 5,603,323 A | * | 2/1997 | Pflugrath et al. ............. | 128/903 |
| 5,676,149 A | * | 10/1997 | Yao .............................. | 600/437 |
| 5,715,823 A | * | 2/1998 | Wood et al. ................. | 600/437 |
| 5,902,241 A | * | 5/1999 | Seyed-Bolorforosh et al. ........................... | 600/443 |
| 5,938,611 A | * | 8/1999 | Muzilla et al. .............. | 600/455 |
| 6,120,449 A | * | 9/2000 | Snyder et al. ............... | 600/447 |

* cited by examiner

Primary Examiner—Francis J. Jaworski
Assistant Examiner—William Jung
(74) Attorney, Agent, or Firm—John F. Thompson; Patrick K. Batnode (57) ABSTRACT

A remotely located ultrasound beamformer is serviced from a central service facility via a network in a manner that compensates for defective beamformer channels in an ultrasound imaging system at the remote location. The central service facility produces beamformer control software (i.e., beamforming parameters) that is optimized for the existing functional channels. The optimized beamformer control software is generated based on diagnostic feedback received from the remotely located system via the network, and is downloaded to the remote system via the same network.

26 Claims, 7 Drawing Sheets

METHOD AND APPARATUS FOR SERVICING REMOTE ULTRASOUND BEAMFORMER FROM CENTRAL SERVICE FACILITY

FIELD OF THE INVENTION

This invention relates to servicing of remote medical diagnostic systems from a central service facility via a network and, more particularly, to remote servicing of ultrasound imaging systems via a network.

BACKGROUND OF THE INVENTION

A conventional ultrasound image is composed of multiple image scan lines. A single scan line (or small localized group of scan lines) is acquired by transmitting focused ultrasound energy at a point in the region of interest, and then receiving the reflected energy over time. The focused transmit energy is referred to as a transmit beam. During the time after transmit, one or more receive beamformers coherently sum the energy received by each channel, with dynamically changing phase rotation or delays, to produce peak sensitivity along the desired scan lines at ranges proportional to the elapsed time. The resulting focused sensitivity pattern is referred to as a receive beam. Resolution of a scan line is dependent on the directivity of the associated transmit and receive beam pair.

In a typical ultrasound imaging system, the output signals of the beamformer channels are coherently summed to form a respective pixel intensity value for each sample volume in the object region or volume of interest. These pixel intensity values are log-compressed, scan-converted and then displayed as an image of the anatomy being scanned.

Conventional ultrasound beamformers use dynamic focusing during reception of echoes. With this method, the Conventional ultrasound beamformers use dynamic focusing during reception of echoes. With this method, the beamformation process is optimized for each depth to achieve as good a beamshape as possible (i.e., narrow beamwidth with low sidelobes). In most systems, a single fixed focus is used during transmit beamformation in attempting to maintain a good combined beamshape. In areas away from the transmit beam focus, the beamwidth of the resultant beam widens and the sidelobes increase.

In the manufacture of an ultrasound system, beamformer control is installed in either algorithmic or tabulated form, and is optimized with the assumption that all system channels are functional. If any of the system channels become defective, image quality is degraded due to increased sidelobes in the ultrasound beam. If the degradation is severe enough, or if the customer is sensitive enough to detect the loss in image quality, a service call of high priority is triggered and a field engineer has to travel to the customer site immediately to repair the defective system. Alternatively, the system might detect the defective channels during self-diagnosis and possibly send that information to the service organization through a remote link. Again, in this instance, a field engineer must repair the defective hardware (preferably before the customer detects the defect.) In either instance, the beamformer controller does not utilize the information relating to defective channels in order to minimize their impact on image quality.

Ultrasound imaging systems of the type described above are often called upon to produce reliable and understandable images within demanding schedules and over a considerable useful life. To ensure proper operation, the systems are serviced regularly by highly trained personnel who address imaging problems, configure and calibrate the systems, and perform periodic system checks and software updates. Moreover, service offerings have been supplemented in recent years by service centers capable of contacting scanners at subscribing institutions directly, without need for intervention on the part of the institution personnel. Such centralized servicing is intended to maintain the ultrasound imaging systems in good operational order without necessitating the attention of physicians or radiologists, and is often quite transparent to the institution.

In certain centralized servicing systems, a computerized service center may contact a scanner via a network to check system configurations and operational states, to collect data for report generation, and to perform other useful service functions. Such contacts can be made periodically, such as during system "sweeps", in which a variety of system performance data are collected and stored with historical data for the particular scanner. The data can then be used to evaluate system performance, propose or schedule visits by service personnel, and the like.

Currently available service systems also permit some degree of interaction between service centers and institutions. For example, a known interactive service system facilitates valuable exchanges of information, including reports of system performance, feedback on particular incidents requiring attention, updates of system licenses, software, and imaging protocols, etc. In particular, a platform has been developed that allows a central service facility to exchange information on possible service problems with remotely located scanners, and to retrieve information or data log files from scanners for the purpose of servicing those scanners.

An integrated user-interactive platform for servicing diagnostic equipment at remote locations may be configured in software, hardware, or firmware at the scanner, or may be installed in a central operator's station linking several scanners in a medical facility. The user interface permits service requests to be generated prior to, during, or subsequent to, examinations executed on the diagnostic equipment. The user interface also permits service messaging, report generation and retrieval, etc. The user interface is preferably configured as a network browser, which also facilitates linking the scanner or the central facility control station to a network such as an intranet or the Internet.

The existence of a networked system for allowing centralized servicing of remote scanners makes it possible to modify the beamformer control function in a remote ultrasound imaging system from a central location to compensate for defective beamformer channels.

BRIEF SUMMARY OF THE INVENTION

A system for servicing a remotely located ultrasound beamformer from a central service facility via a network allows a service organization to repair an ultrasound beamformer in a remotely located ultrasound imaging system. Assuming that one or more beamformer channels are defective, the system will provide degraded images. While the system might detect the defective channels, the pre-installed beamformer control software has been optimized assuming all channels to be functional.

The servicing method, in accordance with a preferred embodiment of the invention, produces beamformer control software (i.e., beamforming parameters) that is optimized for the existing functional channels. The beamformer control software is generated at the central service facility based on diagnostic feedback received from the remotely located system via a network. This new beamformer control software is then downloaded to the remote system via the same network. Subsequent operation of the ultrasound imaging system is in accordance with the new beamforming parameters. Although the resulting beam characteristics are not as good as those for a fully functional system, the resulting beam characteristics are drastically improved over those produced by the uncompensated defective system. Therefore, the image quality of the repaired remote system can be almost as good as the quality of a non-defective system.

The method of operation in accordance with a preferred embodiment is implemented as follows. The system controller of each ultrasound imaging system is programmed to perform a diagnostic routine during startup and to transmit the diagnosis results to the central service facility via a network (e.g., the Internet). The diagnosis results are analyzed at the central service facility. A beamformer control server identifies defective channels and generates optimized beamformer control software to compensate for them. In particular, the optimized beamformer control software is designed to reduce sidelobes in the beam profile which would be produced by the beamformer with defective channels. In accordance with the preferred embodiment, the beam profile, i.e., the aperture function, is numerically optimized. The optimized beamformer control software is then downloaded to the remote system with defective beamformer channels via the network.

Eventually, the remote system will require hardware servicing to replace the defective beamformer channels. In the interim however, the impact of the defective channels can be minimized by the transmission via a network of optimized beamformer control software which mitigates the image degradation due to those defects. The result is reduced urgency for the hardware service.

A preferred embodiment of the servicing system comprises a central service facility coupled to a multiplicity of remotely located beamformers via a network. Each beamformer comprises: means for diagnosing the beamformer to determine the state of the beamformer channels; means for transmitting the diagnosis results to the network addressed to the service facility; means for receiving optimized beamformer control software from the network; and means for installing the optimized beamformer control software in the beamformer. The service facility comprises: means for receiving the diagnosis results via the network; means for generating optimized beamformer control software if the diagnosis results indicate presence of one or more defective beamformer channels; and means for transmitting the optimized beamformer control software to the network addressed to the beamformer. The optimized beamformer control software, whether in algorithmic or tabulated form, is formulated to reduce sidelobes in the beam profile produced by the beamformer with defective beamformer channels.

In an alternative preferred embodiment, the system controller of the remote ultrasound imaging system can be programmed to generate its own optimized beamformer control software. There are, however, limitations on available processing power and the ability to check the results.

DETAILED DESCRIPTION OF THE PREFERRED EMBODIMENTS

Figure 1:
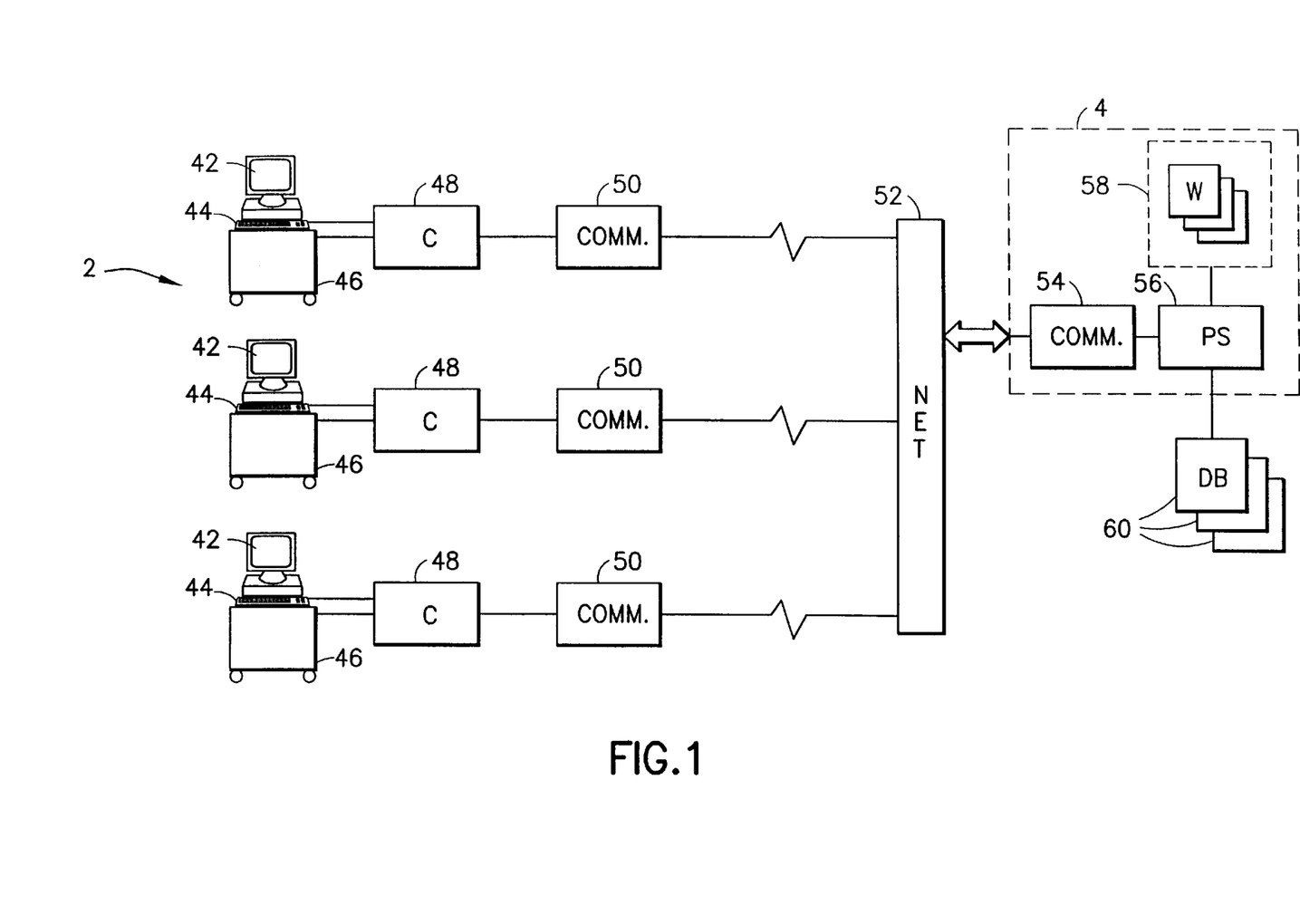
FIG. 1 is a diagrammatical representation of a plurality of remotely located ultrasound imaging systems coupled to a central service facility via a network, for providing centralized service and data interchange between the remote systems and the service facility.

In FIG. 1, a service system is illustrated for providing centralized service to a plurality of ultrasound imaging systems 2 located at different remote sites. The imaging systems are serviced from a centralized service facility 4 via a remote access network 52, which may be the Internet, an intranet, a local area network or any other network.

Each ultrasound imaging system 2 comprises a data acquisition and signal processing unit 46 for transmitting ultrasound signals into a subject of interest, and for acquiring resultant signals which are processed for reconstructing a useful image. The system includes a system controller 48 which regulates operation of unit 46 and which processes acquired signals to reconstruct the image for display by a display subsystem 42. System controller 48 may comprise a central processing unit and associated system memory, and can control the unit 46 to acquire data and process received signals in accordance with software stored in system memory and in accordance with various instructions provided by a system operator via a user interface 44, which may include a keyboard, a mouse, a trackball and various other input devices. The ultrasound imaging system 2 also includes a communications module 50 for transmitting service requests, messages and data between system controller 48 and service facility 4.

Where more than one ultrasound imaging system is provided at a single facility or location, these may be coupled to a management station (not shown) which may be linked directly to controllers for the various imaging systems. The management system may include a computer workstation or personal computer coupled to the system controllers in an intranet configuration, a file-sharing configuration, a client/server arrangement, or any other suitable arrangement. Such a management station typically includes a monitor for viewing system operational parameters, analyzing system utilization, and exchanging service requests and data between the remote facility and the central service facility.

Preferred network configurations for remote access network 52 include both proprietary or dedicated networks, as well as open networks, such as the Internet. Data may be exchanged between the ultrasound imaging systems 2 and central service facility 4 in any suitable format, such as in accordance with the Internet Protocol (IP), the Transmission Control Protocol (TCP), or other known protocols. Moreover, certain of the data may be transmitted or formatted via markup languages, such as the HyperText Markup Language (HTML), or other standard languages.

Within service facility 4, messages, service requests and data are received by communication components 54, which transmit the service data to a service center processing system 56 that manages the receipt, handling and transmission of service data to and from the service facility. In general, processing system 56 may include one or more computers, as well as dedicated hardware or software servers for processing the various service requests and for receiving and transmitting the service data. Service facility 4 also includes a bank of operator workstations 58, which may be staffed by service engineers who address the service requests and provide off-line and on-line service to the diagnostic systems in response to the service requests. Processing system 56 may also be linked to a system of databases or other processing systems 60 at or remote from service facility 4. Such databases and processing systems may include extensive database information on operating parameters, service histories, etc., both for particular subscribing scanners and for extended populations of diagnostic equipment. Such databases may be employed both for servicing particular diagnostic systems and for tracking such servicing, as well as for deriving comparison data for use in servicing a particular system or a family of systems.

Figure 2:
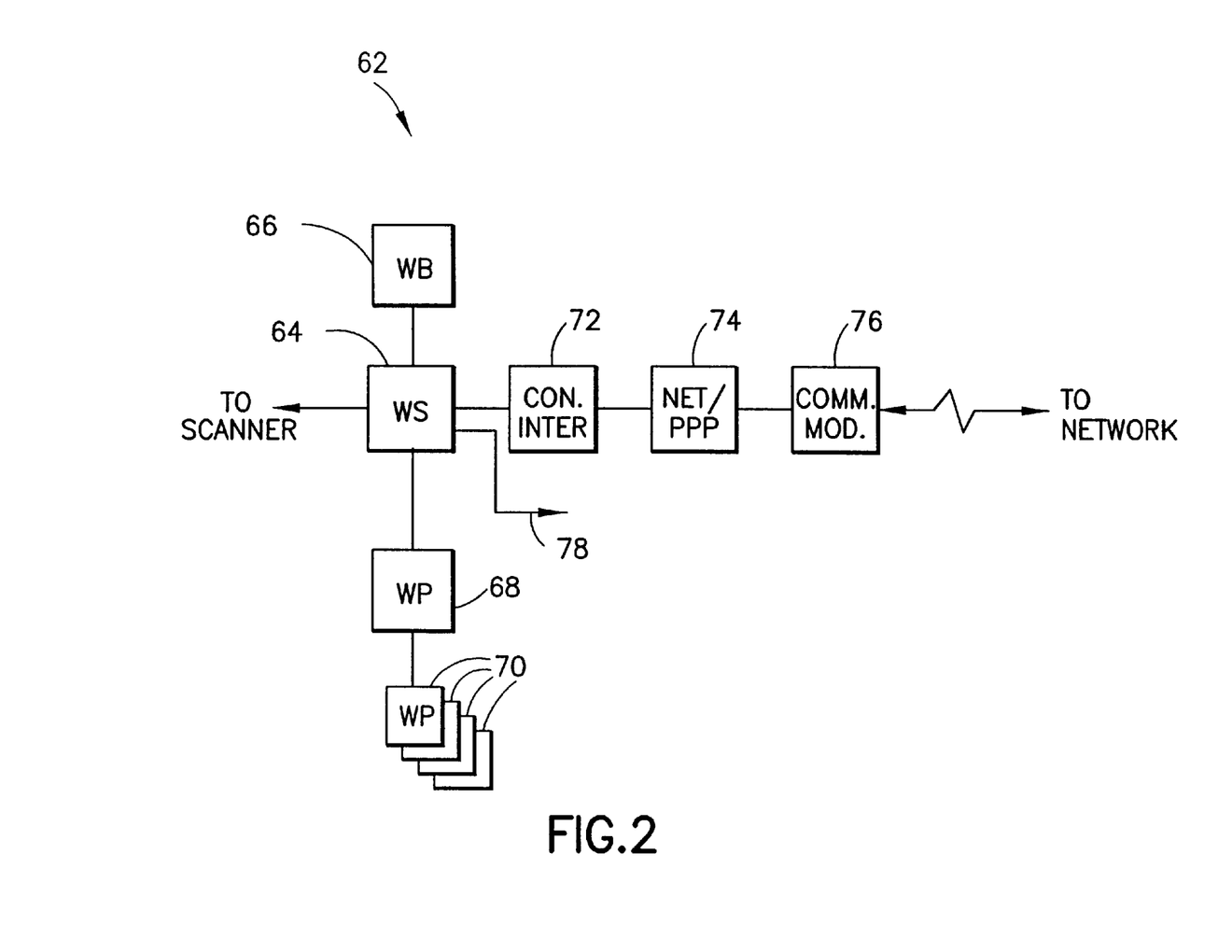
FIG. 2 is a block diagram of certain functional components within an ultrasound imaging system of the type shown in FIG. 1 for facilitating interactive centralized servicing of the ultrasound imaging system.

Within each ultrasound imaging system 2, a uniform service platform 62, shown in FIG. 2, is provided. Platform 62 includes hardware, firmware, and software components adapted for composing and transmitting service requests, transmitting and receiving service data, establishing network connections, and managing financial or subscriber arrangements between the remote system and the service facility. Each platform 62 is preferably integrated into the system controller of the imaging system. These platforms provide a uniform graphical user interface at each imaging system. The platforms enable the service facility to interface directly with the control circuitry of the individual scanners, as well as with memory devices at the scanners, to access image, log and similar files needed for rendering requested or subscribed services. Where a management station is provided, a similar uniform platform is preferably loaded on the management station to facilitate direct interfacing between the management station and the service facility.

FIG. 2 shows the various functional components comprising a uniform service platform 62 within each remote imaging system 2. This uniform service platform can be employed to facilitate both transmission of diagnostic data from the remote system to the central service facility and downloading of beamformer control software from the service facility to the remote system over a network. The uniform service platform resides as software stored in a web server 64 that facilitates data exchange between the diagnostic system and the service facility, and permits a main web page 68 and series of web pages 70 to be viewed via a web browser 66. Server 64 and browser 66 preferably support HTTP applications, and the browser supports Java applications. Main web page 68 is preferably a markup language page, such as an HTML page displayed for the system user on a monitor of display subsystem 42 (FIG. 1), and is preferably accessible from a normal operating page in which the user may configure examination requests, view the results of examinations, etc., such as via an on-screen icon. Through main web page 68, additional web pages 70 are accessible. Such web pages permit service requests and requests for access to software applications to be composed and transmitted to the central service facility, and facilitate the exchange of other messages, reports, software, protocols, etc. Web server 64 communicates with a network via a modem 76. A connectivity service module 72 provides for interfacing with web server 64. A Point-to-Point Protocol (PPP) module 74 is also provided for transmitting Internet Protocol (IP) packets over remote communication connections. As will be appreciated by those skilled in the art, various other network protocols and components may be employed for facilitating data exchange over a network.

A typical ultrasound imaging system employs beamforming during both transmission and reception. The present invention is directed to provision of optimized beamformer control when an ultrasound imaging system has defective beamforming channels. In accordance with a preferred embodiment of the invention, optimized beamformer control software is sent to the defective system from a central service facility via a network. This feature can be programmed into the system depicted in FIG. 1.

Figure 3:
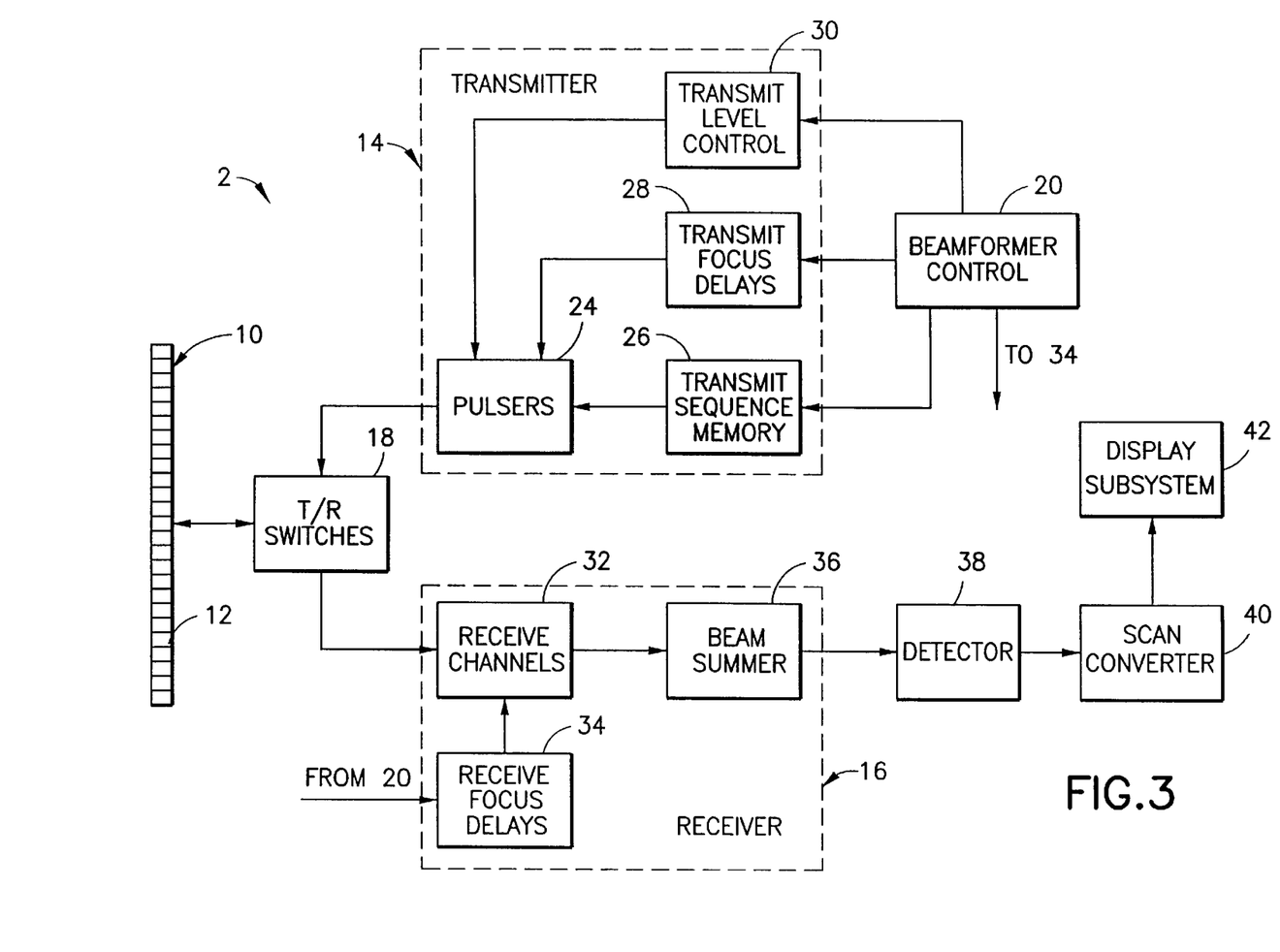
FIG. 3 is a block diagram of the data acquisition and signal processing subsystems of a typical ultrasound imaging system.

FIG. 3 generally depicts a digital real-time ultrasound imaging system of a type which can be repaired using a preferred embodiment of the invention. This imaging system 2 comprises an array 10 of a plurality of separately driven transducer elements 12, each of which produces a burst of ultrasonic energy when energized by a pulsed waveform produced by a transmitter 14. The ultrasonic energy reflected back to transducer array 10 from an object under study is converted to an electrical signal by each receiving transducer element 12 and applied separately to a receiver 16 through a set of transmit/receive (T/R) switches 18. Transmitter 14 and receiver 16 are operated under control of a beamformer controller 20, which is preferably incorporated in the system controller. A complete scan is performed by acquiring a series of echoes in which transmitter 14 is gated ON momentarily to energize each transducer element 12, and the subsequent echo signals produced by each transducer element 12 are applied to receiver 16. A channel may begin reception while another channel is still transmitting. Receiver 16 combines the separate echo signals from each transducer element to produce a single echo signal that is used to produce a line in an image on a monitor of the display subsystem 42.

In the system depicted in FIG. 3, the base waveform transmitted by each transducer element is determined by a digital transmit sequence stored in a transmit sequence memory 26. Each transducer element 12 in the transmit aperture is pulsed by a respective pulser 24 in response to a respective transmit sequence supplied to that pulser from transmit sequence memory 26. The transmit sequence is provided by beamformer controller 20.

Under the direction of beamformer controller 20, transmitter 14 drives transducer array 10 such that the ultrasonic energy is transmitted as a directed focused beam. To accomplish focusing, respective time delays are imparted to pulsers 24 by a transmit focus delay 28, while respective pulse amplitudes are set by a transmit level control (or apodization generator) 30. The transmit focus delays and transmit amplitudes, also provided by the beamformer controller, respectively determine the timing and amplitude of each of the transmit pulses to be generated by pulsers 24. Pulsers 24, in turn, send the transmit pulses to each of elements 12 of transducer array 10 via T/R switches 18. By appropriately adjusting the transmit focus time delays in conventional manner, an ultrasonic beam can be directed and focused at a transmit focal position. The beamformer controller is programmed with algorithms or tables to control transmitter 14 to use spatial apodization and time delays to form a controlled and focused beam when the transducer array elements are fired.

The echo signals produced by each burst of ultrasonic energy reflect from objects located at successive ranges along each ultrasonic beam. Due to differences in the propagation paths between a reflecting point and each transducer element, the echo signals are not detected simultaneously and their amplitudes are not equal. For each transmit, the echo signals from transducer elements 12 are fed to respective receive channels 32 of receiver 16. Under the direction of beamformer controller 20, the receiver tracks the direction of the transmitted beam and imparts the proper receive focus time delays 34 to the received echo signals. The receive focus time delays can be computed in real-time by the beamformer controller or read from a look-up table. The time-delayed receive signals are summed in a receive beam summer 36 for each transmit firing to provide an echo signal that accurately indicates the total ultrasonic energy reflected from a point located at a particular range along the ultrasonic beam.

In a conventional system, the beamsummed receive signals may be bandpass filtered and then supplied to a signal processor or detector 38. The bandpass filter (not shown) will pass the desired signal components. Detector 38 converts the bandpass-filtered receive signals to display data. In the B-mode (grayscale), this is the envelope of the signal, with some additional processing such as edge enhancement and logarithmic compression. A scan converter 40 converts the display data received from detector 38 into data for displaying the desired image. These scan-converted acoustic data are then processed by a video processor within display subsystem 42 and supplied for display on the display system monitor.

The beamformer control software, installed in the system controller in either algorithmic or tabulated form, is optimized with the assumption that all system channels are functional. If any of the system channels become defective, the programmed beamforming parameters become less than optimum and image quality is degraded due to increased sidelobes in the ultrasound beam. In accordance with a preferred embodiment of the invention, the beamformer control software is modified so as to improve the resulting image quality as compared to that of the defective system with unmodified beamformer control software.

In practicing the repair method (and with reference to FIG. 1) the remote system controller 48 is programmed, during startup of ultrasound imaging system 2, to run a diagnostic routine. As part of that routine, the system controller identifies which, if any, beamformer channels are defective. The system controller then sends a report of the diagnostic results to central service facility 4 via network 52. Central processing system 56 then processes the diagnostic results. In particular, the central processing system may comprise a beamformer control server which determines beamforming parameters that minimize the impact of the defective hardware in the remote system. The optimized beamformer control software is then downloaded to the remote system via the network. Although this type of repair results in improved image quality, the resulting image quality is not as good as if a hardware repair had been performed. The relative image quality improvement depends on the number of defective channels. The method disclosed herein can be used as a temporary repair until a hardware repair takes place, to reduce the urgency of the hardware repair.

One way to determine the modified beamforming parameter is to numerically optimize the beam pattern. The optimization takes into account the defective channels. The algorithm optimizes an aperture function which is forced to zero at the locations of defective channels.

A number of optimization approaches are possible. For example, the aperture function can be optimized by numerically minimizing a Cost function which is dependent on the aperture function. More specifically, delay and weighting functions are found which create a beam that follows some desired shape using this numerical optimization method. A Cost function is defined which increases when the actual beam shape deviates from the desired one. Minimizing this Cost function yields the optimal delay and weighting functions. The numerical optimization can be done with any one of a number of algorithms, e.g., using a least squares method.

Figure 4:
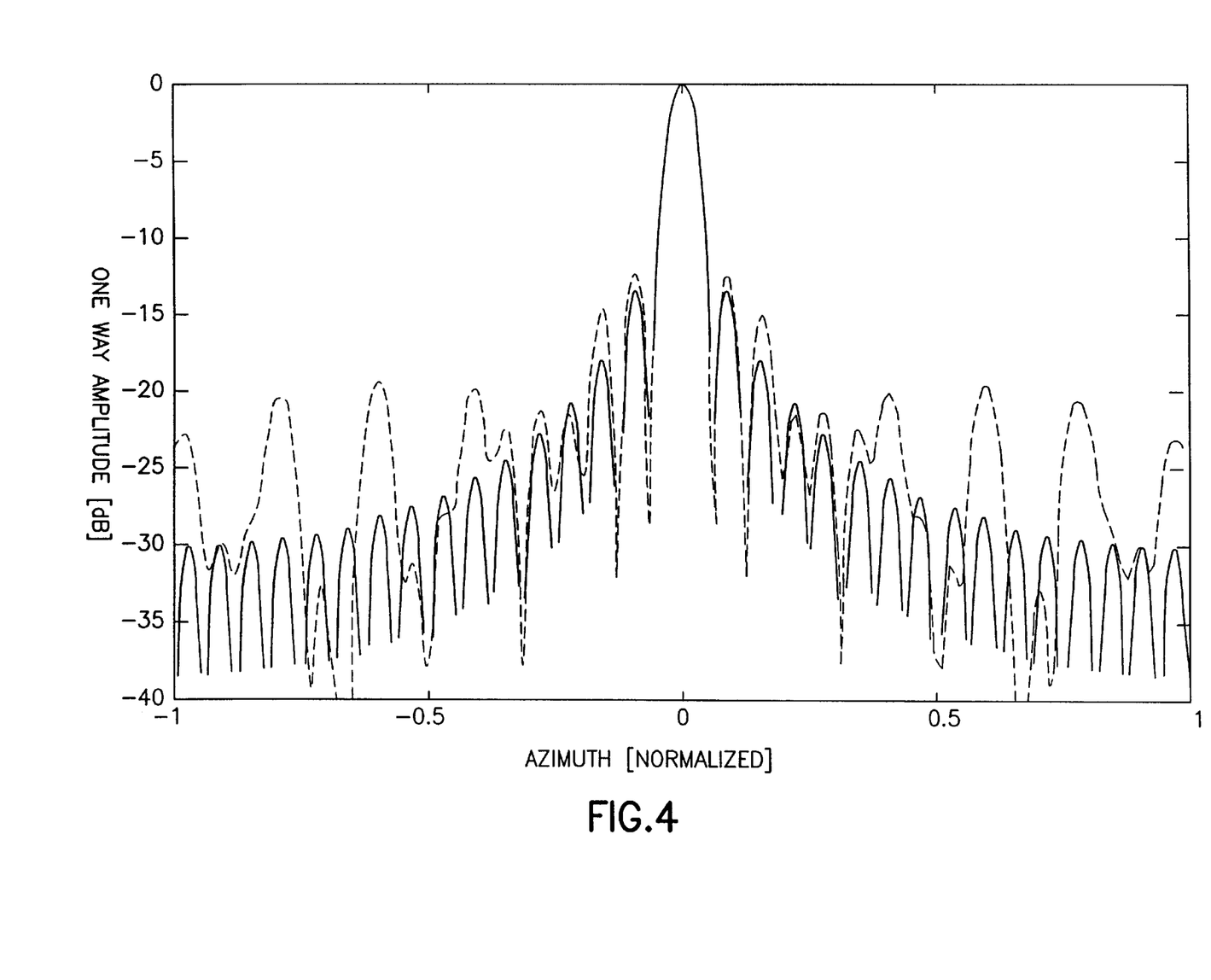
FIG. 4 is a graph of the beam profile for an ideal ultrasound beamformer (i.e., no defective channels) (solid line), and the beam profile for a defective beamformer assuming two defective channels (dashed line).
Figure 5:
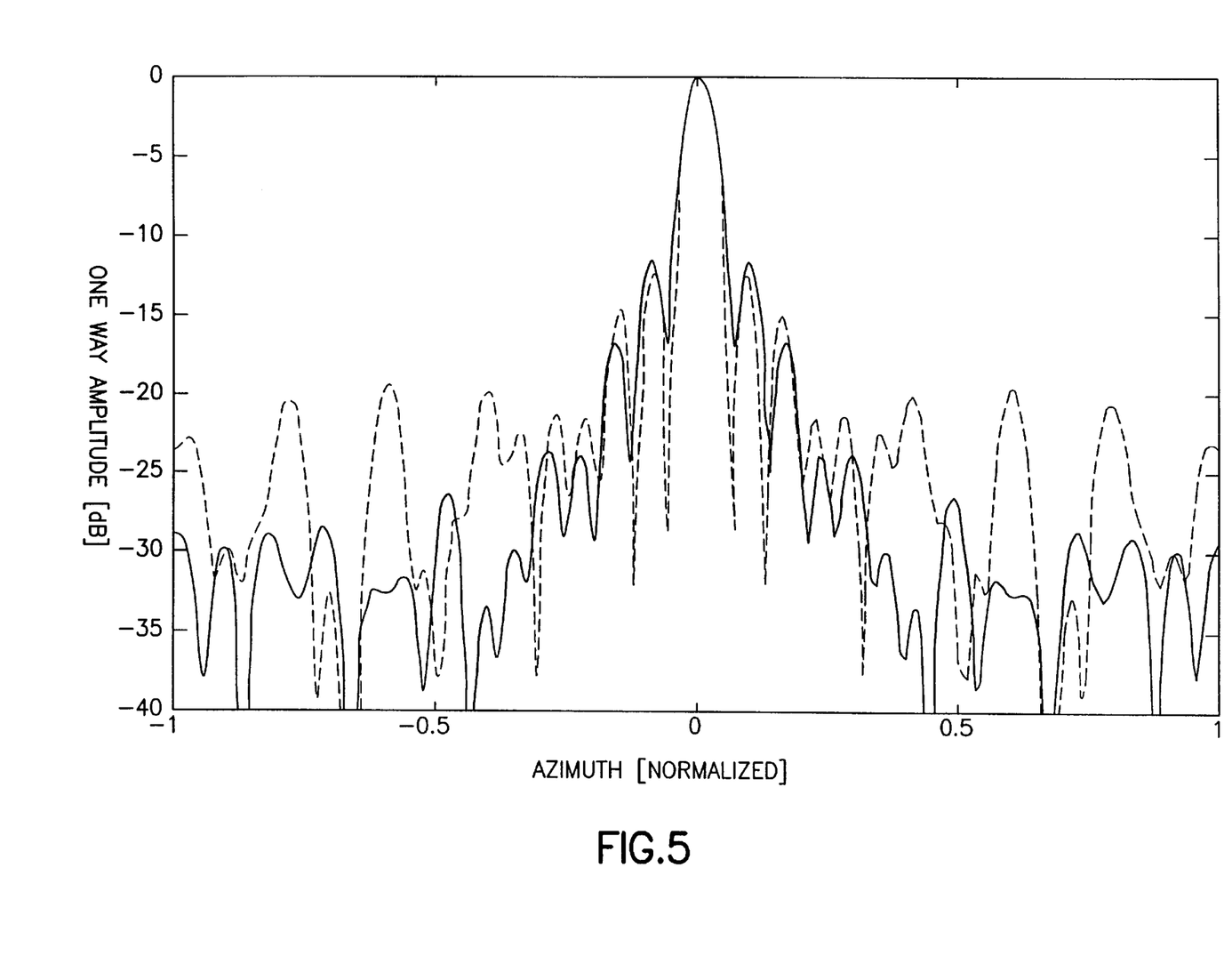
FIG. 5 is a graph of the beam profile for an optimized ultrasound beamformer (i.e., with defective channels) (solid line), and the beam profile for the defective beamformer with two defective channels (dashed line) shown in FIG. 4.

The results presented below have been determined in accordance with the following method. Assuming that an aperture consists of 32 elements and that two elements (numbers 10 and 20) are defective, the beam profiles for the defective and ideal, non-defective apertures are calculated using a narrow-band, far-field approximation. (This simulation type is sufficient to demonstrate the method. When implemented as a service tool, one would select a more accurate simulation method, e.g., wideband, focused). FIG. 4 shows the corresponding graphs for a simulation of one-way beam propagation. The solid line represents the beam profile for an ideal ultrasound beamformer with 32 non-defective channels, while the dashed line represents the beam profile for a defective 32-channel beamformer assuming that channels numbers 10 and 20 are defective. In this example, the sidelobe level of the defective beamformer is increased by 10 dB due to the defective channels. Applying a nonlinear least squares optimization creates the beam profile shown by the solid line in FIG. 5. The optimized profile shows significantly lower sidelobes than the one from the uncorrected defective system. In fact, the sidelobe level is only slightly higher as compared to the ideal system.

In accordance with a preferred embodiment, the aperture weighting and delay functions can be optimized using a numerical optimization method. A Cost function is defined which increases when the actual beam profile deviates from the desired one. Minimizing this Cost function yields the optimal delay and weighting functions. In particular, the desired beam characteristics are transformed into a Cost function for the aperture optimization. To establish the Cost function, the beam profile is needed. Since the beam profile is evaluated a large number of times during the optimization, a narrow-band approximation (phasor) method should be applied.

Figure 6:
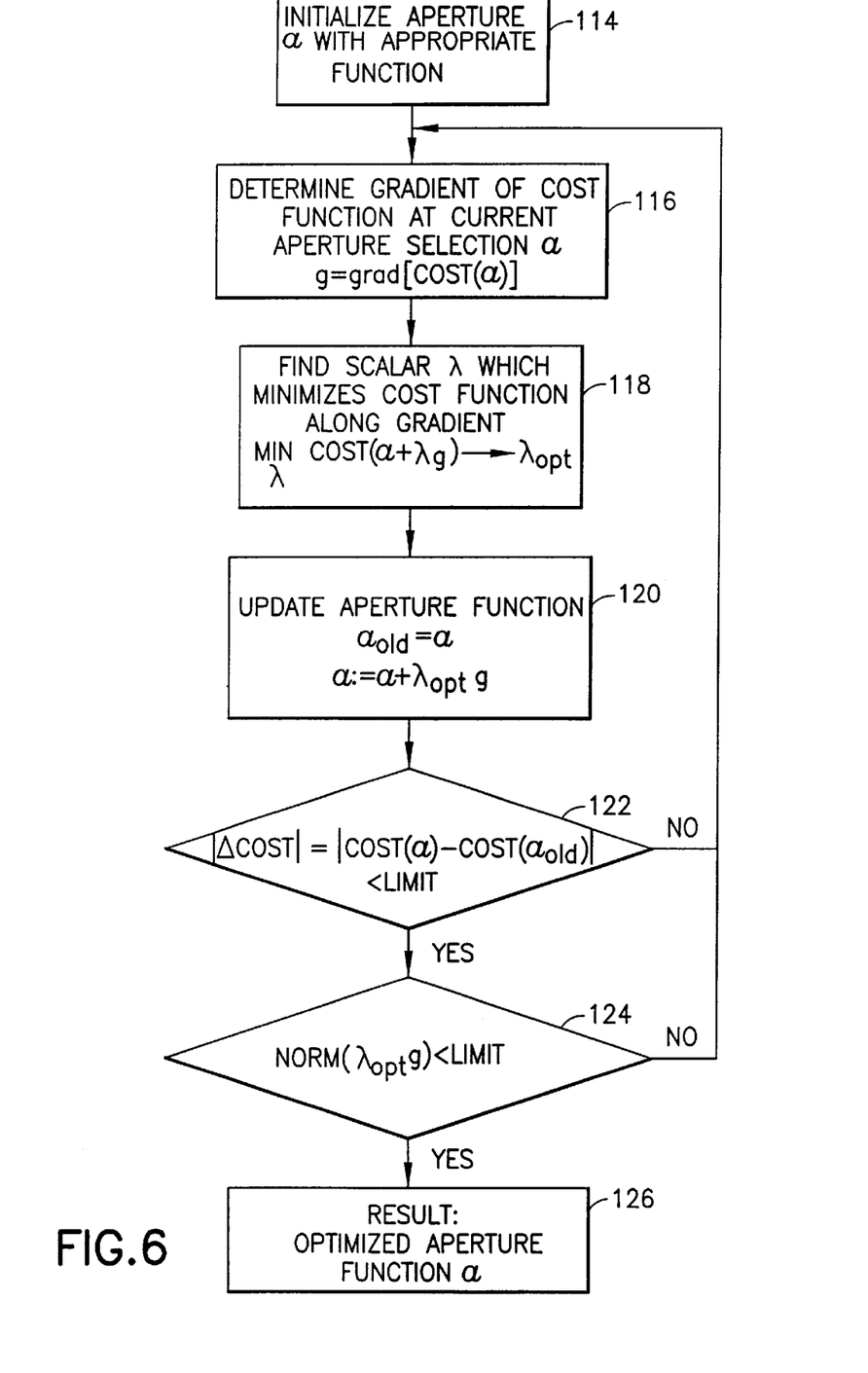
FIG. 6 is a flowchart of a numerical optimization technique in accordance with the preferred embodiment of the invention.

The optimal aperture function can be found by minimizing the Cost function Cost[$a(x)$] subject to certain constraints, where $a(x)$ is the aperture function. The numerical optimization can be done with any of a number of algorithms. For example, an iterative least squares method can be used, as shown in FIG. 6. Since the least squares algorithm only finds a local minimum, an appropriate initial aperture function $a(x)$ must be selected, at step 114. Then, at step 116, the gradient of the Cost function is determined for that aperture function: $g=\text{grad}[\text{Cost}(a)]$. Then, at step 118, a scalar $\lambda$ is found which minimizes the Cost function along the gradient, min Cost($a+\lambda g$), that optimal value being designated $\lambda_{opt}$. The aperture function is updated at step 120, i.e., the old aperture function is stored as $a_{old}$ and a new aperture function is calculated as $a:=a+\lambda_{opt}g$. Then a new Cost function is calculated. A decision is made at step 122 as to whether the absolute value of the difference between the new and old Cost functions is less than a first predetermined limit. These steps are repeated until $|\Delta Cost|$ is less than the first predetermined limit, in which event the determination is made, at step 124, as to whether norm($\lambda_{opt}g$) is less than a second predetermined limit. If it is not, then the foregoing routine is repeated. If nonm($\lambda_{opt}g$) is less than the second predetermined limit, then at step 126 the extant aperture function is adopted as the optimized aperture function. After downloading from the central service facility, the beamformer controller of the ultrasound imaging system controls the transmit levels and transmit focus delays in accordance with the optimized aperture function for each transmit firing.

Several similar optimization methods yield substantially the same result. See, e.g., the numerical optimization methods described in "Optimization Toolbox; User's Guide," The Mathworks, Inc., December (1996) and G. R. Walsh, "Methods of Optimization," John Wiley & Sons (1975). Furthermore, any one of these methods comes in several variations. The present invention is not limited to use of a particular optimization method.

Figure 7:
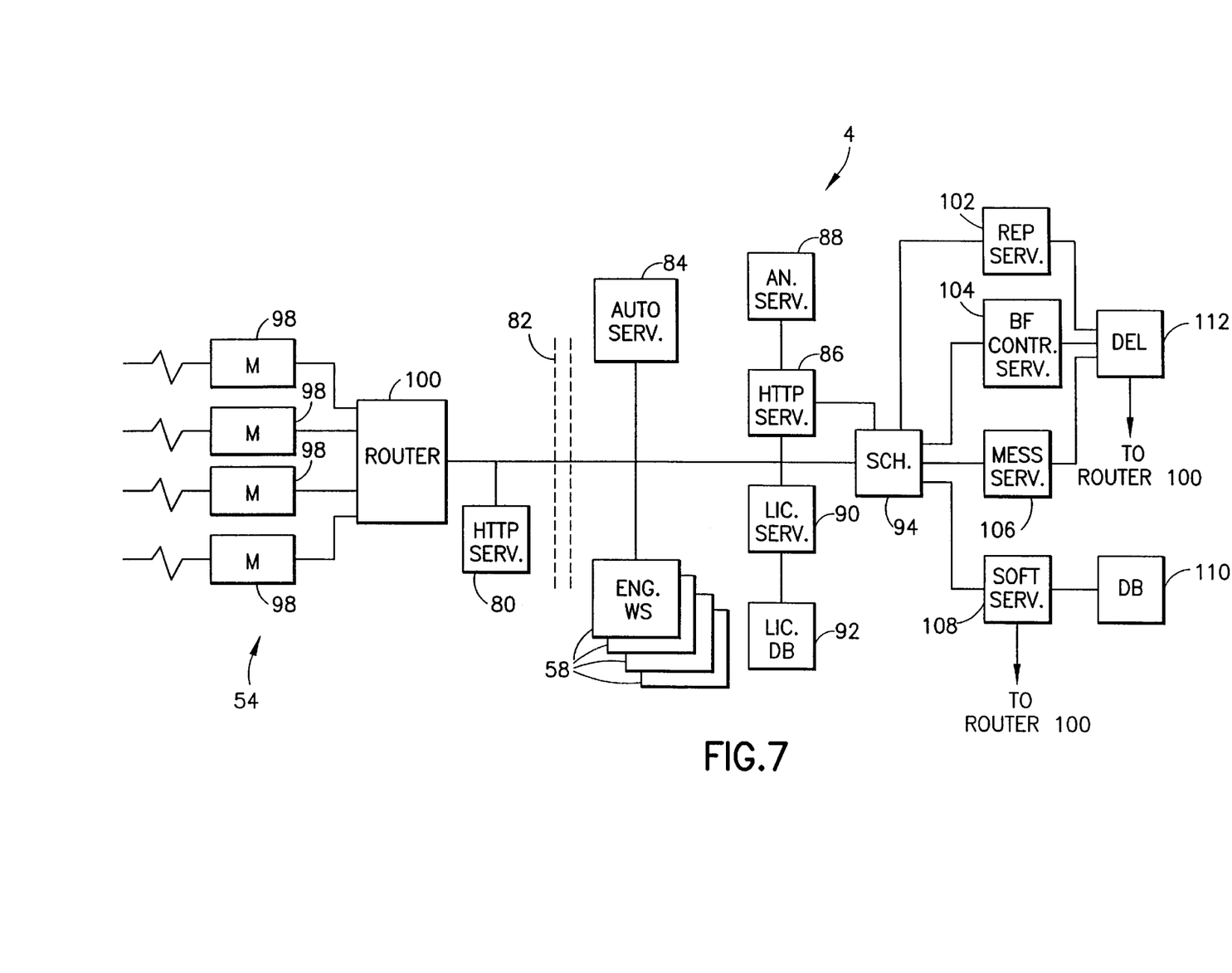
FIG. 7 is a block diagram of certain functional components of an exemplary central service facility for rendering interactive centralized service to a plurality of remotely located medical diagnostic systems.

FIG. 7 illustrates exemplary functional components for a central service facility 4 capable of providing modified beamformer control software in accordance with the preferred embodiments disclosed above. Service facility 4 includes a modem rack comprising a plurality of modems 98 coupled to a router 100 for coordinating data communications with the service facility. A so-called "front office" HTTP service server 80 receives and directs incoming and outgoing transactions with the facility. Server 80 is coupled to the other components of the facility through a firewall 82 for system security. This firewall prevents unauthorized access to the service facility in a manner generally known in the art. In addition, operator workstations 58 are coupled to the port manager for handling service requests and transmitting messages and reports in response to such requests. An automated service unit 84 may also be included in the service facility for automatically responding to certain service requests, sweeping subscribing diagnostic systems for operational parameter data, etc. Automated service unit 84 may operate independently of, or in conjunction with, the interactive service components comprising processing system 56 (FIG. 1).

Behind firewall 82, a so-called "back office" HTTP application server 86 coordinates handling of service requests, messaging, reporting, software transfers, etc. Other servers may be coupled to HTTP application server 86, such as a service analysis server 88 configured to address specific types of service requests. In the illustrated embodiment, processing system 56 includes a license server 90 coupled to a license database 92 for storing, updating and verifying the status of ultrasound imaging system service subscriptions. Handling of service requests, messaging, and reporting is coordinated by a scheduler module 94 coupled to HTTP server 86. Scheduler module 94 coordinates activities of other servers comprising the processing system, such as a report server 102, a beamformer control server 104, a message server 106, and a software download server 108. As will be appreciated by those skilled in the art, servers 102, 104, 106, and 108 are coupled to memory devices (not shown) for storing data such as addresses, log files, message and report files, beamforming parameter tables, applications software, etc. Software server 108 is coupled via one or more data channels to a storage device 110 for containing transmittable software packages which may be sent directly to the diagnostic systems, accessed by the diagnostic systems, or supplied on pay-per-use or purchase basis. Report and message servers 102 and 106 are further coupled to a delivery handling module 112, which is configured to receive outgoing messages, ensure proper connectivity with remote systems, and coordinate transmission of messages to the remote systems via the network.

In accordance with a preferred embodiment of the invention, beamformer control server 104 receives diagnostic results corresponding to a remote imaging system via scheduler module 94. If these results indicate that the remote system has defective beamformer channels, beamformer control server 104 is programmed to generate optimized beamformer control software. The optimized software may take the form of a modified table of beamforming parameters which is downloaded to the remote system via delivery handling module 112. Alternatively, the optimized software may take the form of an algorithm for generating modified beamforming parameters which is downloaded to the remote system. The modified beamforming parameters will be a function of the number and position of the defective channels in the remote system beamformer.

The foregoing functional circuitry may be configured as hardware, firmware, or software on any appropriate computer platform. For example, the functional circuitry of the diagnostic systems may be programmed as appropriate code in a personal computer or workstation, either incorporated entirely in or added to the system scanner. The functional circuitry of the service facility may include additional personal computers or workstations, in addition to a main frame computer in which one or more of the servers, the scheduler, etc. are configured. It should be noted that web server 64 included in the uniform platform shown in FIG. 2 includes unique system identification data which supplement the information provided by the user. The unique system identification data are automatically sent to the service center along with the results of the diagnosis of the beamformer channels, thereby enabling the service facility to determine whether the ultrasound imaging system needing repair service is authorized to receive that service.

In accordance with a further aspect of the invention, the service facility may sweep a selected set of diagnostic systems for the results of self-diagnosis routines run by the system controllers. As used herein, the term "sweep" refers generally to a process of connecting system components, such as via a network connection, identifying desired data, and transmitting the data, either in an "upload" or a "download" scenario, depending upon the nature of the data and their use in servicing a system. Such sweeps may occur on regularly scheduled bases, at desired times (e.g., at off-peak utilization times) or on demand by a system user or a system application.

In accordance with an alternative preferred embodiment, the service procedure disclosed herein may be entirely embedded in the system controller of the remote system. If the beamformer control optimization can be done autonomously, then it may be carried out by the system controller. There are, however, limitations on available processing power and the ability to check the results.

The disclosed method is intended for medical ultrasonic imaging. However, due to its nature, the method is also applicable to other coherent imaging methods (e.g. radar, SLR or microwave).

While only certain preferred features of the invention have been illustrated and described, many modifications and changes will occur to those skilled in the art. It is, therefore, to be understood that the appended claims are intended to cover all such modifications and changes as fall within the true spirit of the invention.

What is claimed is:

1. A method for servicing a beamformer located at a remote site from a service facility located at a central site, said beamformer comprising beamformer channels and beamformer control software, said method comprising the steps of:

diagnosing said beamformer at said remote site to obtain diagnostic results representing the state of beamformer channels in said beamformer;

transmitting said diagnostic results to said service facility at said central site;

if said diagnostic results indicate presence of one or more defective beamformer channels, generating optimized beamformer control software at said service facility which compensates for said defective beamformer channels to reduce sidelobes; and installing said optimized beamformer control software in said beamformer.

2. The method as recited in claim 1, further comprising the step of transmitting said optimized beamformer control software from said service facility to said beamformer.

3. The method as recited in claim 2, wherein the step of transmitting said optimized beamformer control software comprises transmitting via a network.

4. The method as recited in claim 3, wherein the step of transmitting said diagnostic results comprises transmitting via said network.

5. The method as recited in claim 1, wherein the step of generating said optimized beamformer control software is performed using a numerical optimization.

6. The method as recited in claim 5, wherein said numerical optimization is iterative.

7. The method as recited in claim 1, wherein the diagnosing step is performed during startup of said beamformer.

8. A remotely serviceable system comprising a central service facility coupled to a multiplicity of remotely located beamformers via a network, wherein each of said beamformers comprises:

means for diagnosing said beamformers at said remote site to obtain diagnostic results representing the state of beamformer channels in said beamformer;

means for transmitting said diagnostic results to said network addressed to said service facility and for receiving optimized beamformer control software from said network, said means for diagnosing said beamformers also comprising means for installing said optimized beamformer control software in said beamformer:

wherein said service facility comprises:

means for receiving said diagnosis results via said network;

means for generating said optimized beamformer control software if said diagnostic results indicate presence of one or more defective beamformer channels, said optimized beamformer control software being formulated to compensate for said defective beamformer channels to reduce sidelobes; and means for transmitting said optimized beamformer control software to said network addressed to said beamformer.

9. The system as recited in claim 8, wherein said beamformer comprises a multiplicity of piezoelectric ultrasound transducing elements.

10. The system as recited in claim 8, wherein said optimized beamformer control software is generated from a numerical optimization.

11. The system as recited in claim 8, wherein said optimized beamformer control software is generated from an iterative numerical optimization.

12. The system as recited in claim 8, wherein said means for diagnosing are adapted to be activated during startup of said beamformer.

13. The system as recited in claim 8, wherein said optimized beamformer control software is in algorithmic form.

14. The system as recited in claim 8, wherein said optimized beamformer control software is in tabulated form.

15. The system as recited in claim 8, wherein said network comprises an intranet.

16. The system as recited in claim 8, wherein said network comprises the Internet.

17. The system as recited in claim 8, wherein said network comprises a local area network.

18. An ultrasound imaging system comprising:

a multiplicity of beamformer channels;

a beamformer controller programmed with beamformer control software for controlling beamforming in said beamformer channels;

means for diagnosing said beamformer channels to obtain diagnostic results representing the state of said beamformer channels;

a communications module for communicating with a network; and means for transmitting said diagnostic results to said communications module and for receiving optimized beamformer control software from said communications module, said means for diagnosing also comprising means for installing said optimized beamformer control software in said beamformer controller.

19. An ultrasound imaging system comprising:

a multiplicity of beamformer channels;

a beamformer controller programmed with beamformer control software for controlling beamforming in said beamformer channels; and means for diagnosing said beamformer channels to identify any defective beamformer channels and for optimizing said beamformer control software in said beamformer controller to compensate for any identified defective channels.

20. The system as recited in claim 19, wherein said optimized beamformer control software is generated from a numerical optimization.

21. A method for servicing, from a service facility located at a central site, a beamformer located at a remote site and having defective beamformer channels, comprising the steps of:

generating optimized beamformer control software at said service facility which compensates for said defective beamformer channels to reduce sidelobes; and downloading said optimized beamformer control software to said beamformer via a network.

22. The method as recited in claim 21, further comprising the steps of:

diagnosing said beamformer at said remote site to obtain diagnostic results representing the state of beamformer channels in said beamformer; and transmitting said diagnostic results to said service facility at said central site via said network.

23. A service facility comprising:

a communications channel for coupling to a network; and a processing system programmed to communicate with, and provide service to, a multiplicity of ultrasound imaging systems coupled to said network, said processing system comprising a beamformer control server programmed to perform the steps of:

processing diagnostic results to identify defective channels in a remote beamformer;

generating optimized beamformer control software which compensates for said defective beamformer channels to reduce sidelobes in a beam profile; and sending said optimized beamformer control software to said communications channel with a network address of said remote beamformer.

24. The service facility as recited in claim 23, wherein said optimized beamformer control software is generated from a numerical optimization.

25. The system as recited in claim 23, wherein said optimized beamformer control software is in algorithmic form.

26. The system as recited in claim 23, wherein said optimized beamformer control software is in tabulated form.

* * * * *